United States Patent
Stewart et al.

(10) Patent No.: US 10,285,755 B2
(45) Date of Patent: *May 14, 2019

(54) MESH-OVERLAYED ABLATION AND MAPPING DEVICE

(71) Applicant: Medtronic Ablation Frontiers LLC, Minneapolis, MN (US)

(72) Inventors: Mark T. Stewart, Lino Lakes, MN (US); Jordon D. Honeck, Maple Grove, MN (US)

(73) Assignee: Medtronic Ablation Frontiers LLC, Minneapolis, MN (US)

( * ) Notice: Subject to any disclaimer, the term of this patent is extended or adjusted under 35 U.S.C. 154(b) by 423 days.

This patent is subject to a terminal disclaimer.

(21) Appl. No.: 15/180,821

(22) Filed: Jun. 13, 2016

(65) Prior Publication Data

US 2016/0278858 A1  Sep. 29, 2016

Related U.S. Application Data

(62) Division of application No. 13/194,180, filed on Jul. 29, 2011, now Pat. No. 9,387,031.

(51) Int. Cl.
*A61B 18/14* (2006.01)
*A61B 18/02* (2006.01)
*A61B 18/00* (2006.01)

(52) U.S. Cl.
CPC .......... *A61B 18/1492* (2013.01); *A61B 18/02* (2013.01); *A61B 2018/0022* (2013.01);
(Continued)

(58) Field of Classification Search
CPC ..... A61B 18/02; A61B 18/0218; A61B 18/14; A61B 18/1492; A61B 2018/00023;
(Continued)

(56) References Cited

U.S. PATENT DOCUMENTS

| 4,813,934 A | 3/1989 | Engelson et al. |
| 4,846,174 A | 7/1989 | Willard et al. |

(Continued)

FOREIGN PATENT DOCUMENTS

| EP | 0957758 B1 | 3/2004 |
| EP | 0896211 B1 | 10/2004 |

(Continued)

OTHER PUBLICATIONS

Avitall, B., et al., "New Cryotechnology for Electrical Isolation of the Pulmonary Veins", Journal of Cardiovascular Electrophysiology, vol. 14, No. 3, Mar. 2003, pp. 281-286.
(Continued)

*Primary Examiner* — Michael F Peffley
*Assistant Examiner* — Khadijeh A Vahdat
(74) *Attorney, Agent, or Firm* — Christopher & Weisberg, P.A.

(57) ABSTRACT

A medical system, including a catheter body, an elongate body disposed in the catheter body; an expandable element having a proximal portion coupled to the catheter body and a distal portion coupled to the elongate body, the distal portion of the expandable element defining the distal-most portion of the medical device; a mesh or array of longitudinal splines substantially surrounding the expandable element, at least a portion of the mesh or splines being electrically conductive; and a coolant source in fluid communication with the expandable element.

16 Claims, 4 Drawing Sheets

(52) U.S. Cl.
CPC ............ *A61B 2018/00357* (2013.01); *A61B 2018/00577* (2013.01); *A61B 2018/00613* (2013.01); *A61B 2018/00797* (2013.01); *A61B 2018/00815* (2013.01); *A61B 2018/00821* (2013.01); *A61B 2018/00994* (2013.01); *A61B 2018/0212* (2013.01); *A61B 2018/0237* (2013.01); *A61B 2018/0262* (2013.01); *A61B 2018/1437* (2013.01)

(58) Field of Classification Search
CPC .. A61B 2018/0022; A61B 2018/00285; A61B 2018/00577; A61B 2018/00744; A61B 2018/0262
USPC ..................................................... 606/21–52
See application file for complete search history.

(56) References Cited

U.S. PATENT DOCUMENTS

| | | | |
|---|---|---|---|
| 4,968,300 A | 11/1990 | Moutafis et al. | |
| 5,281,213 A | 1/1994 | Milder et al. | |
| 5,397,308 A | 3/1995 | Ellis et al. | |
| 5,398,683 A | 3/1995 | Edwards et al. | |
| 5,423,755 A | 6/1995 | Kesten et al. | |
| 5,447,497 A | 9/1995 | Sogard et al. | |
| 5,472,441 A | 12/1995 | Edwards et al. | |
| 5,487,385 A | 1/1996 | Avitall | |
| 5,575,766 A | 11/1996 | Swartz et al. | |
| 5,584,803 A | 12/1996 | Stevens et al. | |
| 5,617,854 A | 4/1997 | Munsif | |
| 5,673,695 A | 10/1997 | McGee et al. | |
| 5,725,523 A | 3/1998 | Mueller | |
| 5,772,681 A | 6/1998 | Leoni | |
| 5,776,129 A | 7/1998 | Mersch | |
| 5,868,735 A | 2/1999 | Lafontaine | |
| 5,910,154 A | 6/1999 | Tsugita et al. | |
| 5,928,193 A | 7/1999 | Campbell | |
| 5,938,660 A | 8/1999 | Swartz et al. | |
| 5,964,778 A | 10/1999 | Fugoso et al. | |
| 5,971,979 A | 10/1999 | Joye et al. | |
| 5,980,486 A | 11/1999 | Enger | |
| 6,012,457 A | 1/2000 | Lesh | |
| 6,024,740 A | 2/2000 | Lesh et al. | |
| 6,036,697 A | 3/2000 | DiCaprio | |
| 6,088,614 A | 7/2000 | Swanson | |
| 6,161,543 A | 12/2000 | Cox et al. | |
| 6,164,283 A | 12/2000 | Lesh | |
| 6,179,810 B1 | 1/2001 | Wantink et al. | |
| 6,179,827 B1 | 1/2001 | Davis et al. | |
| 6,214,002 B1 | 4/2001 | Fleischman et al. | |
| 6,233,491 B1 | 5/2001 | Kordis et al. | |
| 6,237,604 B1 | 5/2001 | Burnside et al. | |
| 6,241,754 B1 | 6/2001 | Swanson et al. | |
| 6,245,064 B1 | 6/2001 | Lesh et al. | |
| 6,254,599 B1 | 7/2001 | Lesh et al. | |
| 6,283,959 B1 | 9/2001 | Lalonde et al. | |
| 6,290,696 B1 | 9/2001 | Lafontaine | |
| 6,305,378 B1 | 10/2001 | Lesh | |
| 6,312,407 B1 | 11/2001 | Zadno-Azizi et al. | |
| 6,325,797 B1 | 12/2001 | Stewart et al. | |
| 6,355,029 B1 | 3/2002 | Joye et al. | |
| 6,387,092 B1 | 5/2002 | Burnside et al. | |
| 6,416,511 B1 | 7/2002 | Lesh et al. | |
| 6,428,536 B2 | 8/2002 | Panescu et al. | |
| 6,432,102 B2 | 8/2002 | Joye et al. | |
| 6,471,694 B1 | 10/2002 | Kudaravalli et al. | |
| 6,502,576 B1 | 1/2003 | Lesh | |
| 6,514,245 B1 | 2/2003 | Williams et al. | |
| 6,514,249 B1 | 2/2003 | Maguire et al. | |
| 6,517,514 B1 | 2/2003 | Campbell | |
| 6,517,533 B1 | 2/2003 | Swaminathan | |
| 6,572,612 B2 | 6/2003 | Stewart et al. | |
| 6,575,966 B2 | 6/2003 | Lane et al. | |
| 6,578,579 B2 | 6/2003 | Burnside et al. | |
| 6,585,733 B2 | 7/2003 | Wellman | |
| 6,595,988 B2 | 7/2003 | Wittenberger et al. | |
| 6,602,276 B2 | 8/2003 | Dobak, III et al. | |
| 6,626,861 B1 | 9/2003 | Hart et al. | |
| 6,640,120 B1 | 10/2003 | Swanson et al. | |
| 6,641,511 B2 | 11/2003 | Patel et al. | |
| 6,645,234 B2 | 11/2003 | Evans et al. | |
| 6,648,878 B2 | 11/2003 | Lafontaine | |
| 6,648,879 B2 | 11/2003 | Joye et al. | |
| 6,648,883 B2 | 11/2003 | Francischelli et al. | |
| 6,652,515 B1 | 11/2003 | Maguire et al. | |
| 6,659,981 B2 | 12/2003 | Stewart et al. | |
| 6,666,858 B2 | 12/2003 | Lafontaine | |
| 6,685,732 B2 | 2/2004 | Kramer | |
| 6,689,128 B2 | 2/2004 | Sliwa, Jr. et al. | |
| 6,702,811 B2 | 3/2004 | Stewart et al. | |
| 6,738,673 B2 | 5/2004 | Desai | |
| 6,740,104 B1 | 5/2004 | Solar et al. | |
| 6,755,822 B2 | 6/2004 | Reu et al. | |
| 6,758,847 B2 | 7/2004 | Maguire | |
| 6,780,183 B2 | 8/2004 | Jimenez, Jr. et al. | |
| 6,811,550 B2 | 11/2004 | Holland et al. | |
| 6,837,886 B2 | 1/2005 | Collins et al. | |
| 6,875,209 B2 | 4/2005 | Zvuloni et al. | |
| 6,929,639 B2 | 8/2005 | Lafontaine | |
| 6,952,615 B2 | 10/2005 | Satake | |
| 6,989,009 B2 | 1/2006 | Lafontaine | |
| 7,029,470 B2 | 4/2006 | Francischelli et al. | |
| 7,097,641 B1 | 8/2006 | Arless et al. | |
| 7,097,643 B2 | 8/2006 | Cornelius et al. | |
| 7,137,395 B2 | 11/2006 | Fried et al. | |
| 7,226,446 B1 | 6/2007 | Mody et al. | |
| 7,255,695 B2 * | 8/2007 | Falwell | A61B 5/0422 600/374 |
| 7,465,300 B2 | 12/2008 | Arless et al. | |
| 7,479,141 B2 | 1/2009 | Kleen et al. | |
| 7,519,410 B2 | 4/2009 | Taimisto et al. | |
| 7,540,853 B2 | 6/2009 | Hayzelden | |
| 7,655,005 B2 | 2/2010 | Bhola | |
| 7,674,256 B2 | 3/2010 | Marrouche et al. | |
| 7,706,894 B2 | 4/2010 | Stewart et al. | |
| 7,740,627 B2 | 6/2010 | Gammie et al. | |
| 2002/0032406 A1 | 3/2002 | Kusleika | |
| 2002/0035361 A1 | 3/2002 | Houser et al. | |
| 2002/0045894 A1 | 4/2002 | Joye et al. | |
| 2002/0087151 A1 | 7/2002 | Mody et al. | |
| 2002/0128636 A1 | 9/2002 | Chin et al. | |
| 2002/0183691 A1 | 12/2002 | Callister | |
| 2002/0188325 A1 | 12/2002 | Hill et al. | |
| 2003/0009160 A1 | 1/2003 | Carroll et al. | |
| 2003/0125721 A1 | 7/2003 | Yon et al. | |
| 2003/0153905 A1 | 8/2003 | Edwards et al. | |
| 2003/0158516 A1 | 8/2003 | Wholey et al. | |
| 2003/0199861 A1 | 10/2003 | Lafontaine | |
| 2004/0034344 A1 | 2/2004 | Ryba | |
| 2004/0073203 A1 | 4/2004 | Yu et al. | |
| 2004/0073301 A1 | 4/2004 | Donlon et al. | |
| 2004/0158237 A1 | 8/2004 | Abboud et al. | |
| 2004/0215186 A1 | 10/2004 | Cornelius et al. | |
| 2004/0225342 A1 | 11/2004 | Callister | |
| 2005/0020901 A1 | 1/2005 | Belson et al. | |
| 2005/0070887 A1 | 3/2005 | Taimisto et al. | |
| 2005/0182393 A1 | 8/2005 | Abboud et al. | |
| 2005/0182395 A1 | 8/2005 | Lafontaine | |
| 2005/0256521 A1 | 11/2005 | Kozel | |
| 2006/0041277 A1 * | 2/2006 | Deem | A61N 1/0551 607/3 |
| 2006/0247611 A1 | 11/2006 | Abboud et al. | |
| 2006/0271032 A1 | 11/2006 | Chin et al. | |
| 2006/0271093 A1 | 11/2006 | Holman et al. | |
| 2007/0078453 A1 | 4/2007 | Johnson et al. | |
| 2007/0093710 A1 | 4/2007 | Maschke | |
| 2007/0233222 A1 | 10/2007 | Roeder et al. | |
| 2008/0009851 A1 | 1/2008 | Wittenberger et al. | |
| 2008/0015561 A1 | 1/2008 | Abboud et al. | |
| 2008/0091180 A1 | 4/2008 | Abboud et al. | |
| 2008/0103493 A1 | 5/2008 | Abboud et al. | |
| 2008/0281391 A1 | 11/2008 | MacAdam et al. | |
| 2009/0228003 A1 | 9/2009 | Sinelnikov | |

(56) References Cited

U.S. PATENT DOCUMENTS

| | | |
|---|---|---|
| 2009/0248014 A1 | 10/2009 | Shachar et al. |
| 2009/0299355 A1 | 12/2009 | Bencini et al. |
| 2009/0306641 A1 | 12/2009 | Govari et al. |
| 2010/0114269 A1 | 5/2010 | Wittenberger et al. |
| 2010/0114287 A1 | 5/2010 | Privitera et al. |
| 2010/0137704 A1 | 6/2010 | Vij et al. |
| 2010/0168557 A1 | 7/2010 | Deno et al. |
| 2011/0208096 A1* | 8/2011 | Demarais ............. A61F 7/123 601/3 |
| 2012/0029496 A1* | 2/2012 | Smith ................. A61B 18/02 606/21 |
| 2012/0035601 A1 | 2/2012 | Wittenberger |
| 2012/0101485 A1 | 4/2012 | Wittenberger |
| 2012/0109118 A1 | 5/2012 | Lalonde et al. |
| 2012/0283713 A1 | 11/2012 | Mihalik et al. |

FOREIGN PATENT DOCUMENTS

| | | |
|---|---|---|
| EP | 1383426 B1 | 12/2008 |
| WO | 94/06349 A1 | 3/1994 |
| WO | 96/34571 A1 | 11/1996 |
| WO | 99/02096 A1 | 1/1999 |
| WO | 00/07657 A1 | 2/2000 |
| WO | 0042932 A1 | 7/2000 |
| WO | 01/22897 A1 | 4/2001 |
| WO | 2001060441 A1 | 8/2001 |
| WO | 02/07628 A2 | 1/2002 |
| WO | 02/083196 A2 | 10/2002 |
| WO | 03020334 A2 | 3/2003 |
| WO | 03/026719 A2 | 4/2003 |
| WO | 03039338 A2 | 5/2003 |
| WO | 2005/067668 A2 | 7/2005 |
| WO | 2005/089853 A1 | 9/2005 |
| WO | 2006058251 A2 | 6/2006 |
| WO | 2006/118725 A1 | 11/2006 |
| WO | 2008000065 A1 | 1/2008 |
| WO | 2009/065042 A2 | 5/2009 |
| WO | 2009/140067 A1 | 11/2009 |
| WO | 2010002888 A2 | 1/2010 |
| WO | 2010006229 A1 | 1/2010 |
| WO | 2010/067360 A2 | 6/2010 |

OTHER PUBLICATIONS

Shu et al., "Combined Radiofrequency Ablation-Cooling Catheter for Reversible Cryothermal Mapping and Ablation", Journal of Interventional Cardiac Electrophysiology, 1997, 1:139-144.

Khairy et al., "A Novel Hybrid Transcatheter Ablation System That Combines Radiofrequency and Cryoenergy", J Cardiovasc Electrophysiol, vol. 19, pp. 188-193, Feb. 2008.

Parvez et al., "Comparison of Lesion Sizes Produced by Cryoablation and Open Irrigation Radiofrequency Ablation Catheters", J Cardiovasc Electrophysiol, vol. 19, pp. 528-534, May 2008.

* cited by examiner

# MESH-OVERLAYED ABLATION AND MAPPING DEVICE

CROSS-REFERENCE TO RELATED APPLICATION

This application is a divisional of patent application Ser. No. 13/194,180, filed Jul. 29, 2011, Now, U.S. Pat. No. 9,387,031 entitled MESH-OVERLAYED ABLATION AND MAPPING DEVICE, the entirety of which is incorporated herein by reference.

STATEMENT REGARDING FEDERALLY SPONSORED RESEARCH OR DEVELOPMENT n/a

FIELD OF THE INVENTION

The present invention relates to medical systems and methods for electrophysiological procedures and treatment, and in particular to cardiac tissue mapping and ablation.

BACKGROUND OF THE INVENTION

Medical procedures are available for treating a variety of cardiovascular maladies, such as cardiac arrhythmias including atrial fibrillation, and other irregularities in the transmission of electrical impulses through the heart. As an alternative to open-heart surgery, many medical procedures are performed using minimally invasive surgical techniques, where one or more slender implements are inserted through one or more small incisions into a patient's body. Such procedures may involve the use of catheters or probes having multiple sensors, electrodes, or other measurement and treatment components to treat the diseased area of the heart, vasculature, or other tissue. Minimally-invasive devices are desirable for various medical and surgical applications because they allow for precise treatment of localized discrete tissues that are otherwise difficult to access. For example, catheters may be easily inserted and navigated through the blood vessels and arteries, allowing non-invasive percutaneous access to areas of the body selected for treatment, while other minimally-invasive probes or instruments may be inserted into small openings and directed through targeted anatomy without significant impact or disruption to surrounding tissue.

One such example of a minimally invasive therapy involves the treatment of cardiac arrhythmias or irregular heartbeats in which physicians employ specialized cardiac assessment and treatment devices, such as mapping catheters and ablation catheters, to gain access to, diagnose, and treat interior regions of a patient's body. Such devices may include energized electrodes or other ablation assemblies to create lesions or other anatomical effects that disrupt or block electrical pathways through the targeted tissue.

In the treatment of cardiac arrhythmias, a specific area of cardiac tissue having aberrant electrically conductive pathways is typically initially identified for subsequent treatment. This localization or identification can include first using a medical device such as a mapping catheter to obtain a baseline electrophysiological map of electrical activity in selected tissue. After mapping and diagnosing aberrant tissue, a physician may decide to treat the patient by ablating the tissue. An ablation procedure may involve creating one or more lesions to electrically isolate tissue believed to be the source of an arrhythmia. One type of ablation is the cryotreatment or cryogenic ablation, which entails creating cold temperatures at specific regions of the body or contacting tissue with cold treatment devices to transfer heat from the targeted tissue to the cryogenic element, thus cooling and/or ablating the tissue. Other treatments may include radiofrequency tissue ablation or electroporation procedures.

Such treatments may require first repositioning or removing a mapping catheter before placing a second medical device or ablation catheter into contact with the tissue to be treated. Following the ablation procedure, the physician may desire to asses or confirm the efficacy of the treatment by obtaining a second electrophysiological map of the tissue region. This subsequent mapping procedure may involve removal or manipulation of the ablation medical device to allow the desired positioning of the mapping device adjacent to the tissue that was previously treated.

Each device exchange or manipulation represents an added risk to the patient as inserting and removing catheters in the vasculature carries a number of inherent risks, possibly including embolism. Exchanging these various catheters during a procedure can cause inaccuracies or movement in the placement and location of the distal tip a device with respect to the tissue to be mapped or ablated, and may further add to the time required to perform the desired treatment. These potential inaccuracies and extended duration of the particular procedure further increase the risk to the patient undergoing treatment. Accordingly, it would be desirable to provide an integrated apparatus and method of use thereof for both diagnosing aberrant electrical pathways and treating those detected pathways.

In addition, placing and maintaining a medical device in the desired position with correct alignment and positive contact with the selected tissue may enhance a mapping and ablation treatment and its likelihood of success. It is therefore desirable to provide apparatus and method of use to verify the position of a medical device, positive contact and alignment with the selected tissue, and to contemporaneously evaluate the medical treatment.

SUMMARY OF THE INVENTION

The present invention advantageously provides methods and systems for diagnosing aberrant electrical pathways, treating those detected pathways, and verifying the position, contact, and/or orientation of the system.

In particular, a medical system is provided, including a catheter body, an elongate body disposed in the catheter body; an expandable element having a proximal portion coupled to the catheter body and a distal portion coupled to the elongate body, the distal portion of the expandable element defining the distal-most portion of the medical device; a mesh or array of splines or arms substantially surrounding the expandable element, at least a portion of the mesh or arms are electrically conductive; and a coolant source may also be in fluid communication with the expandable element. The elongate body may be longitudinally movable within the catheter body and may define a guide wire lumen. The system may include a fluid injection lumen coupling the coolant source to an interior of the expandable element; a fluid distribution element coupled to the fluid injection lumen, the fluid distribution element being controllably rotatable and translatable within the interior of the expandable element, where the fluid distribution element may include a valve movably coupled to the elongate body; an impedance assessment unit coupled to the mesh; and/or a high-voltage, pulsed signal generator in electrical communication with the mesh. The mesh or arms may include at least one electrically-insulated portion and at least one electrically-conductive portion; an electrically-conductive portion disposed between two electrically-insulated portions; and/or an electrically-insulated portion disposed between two electrically-conductive portions. The mesh or array of arms may also include a plurality of independent electrodes to allow collection of local electrical signals. The mesh may be controllably transitionable from a first shape to a second shape, where the expansion of the expandable element is inhibited at least in part by the mesh. The mesh may include a plurality of interwoven wires that are at least partially electrically-insulated and/or may include a plurality of thermocouples or thermistors. The system may include a sheath slidably coupled to at least a portion of the catheter body.

A method of treating a substantially continuous tissue region is provided, including positioning a medical device adjacent the tissue region, the medical device including an expandable element and an electrically conductive mesh or array of splines substantially enclosing the expandable element; contacting the substantially continuous tissue region with a distal face of the expandable element; measuring an electrical signal from the tissue region with the mesh; and ablating at least a portion of the tissue region with at least one of the expandable element and the mesh. Ablating at least a portion of the tissue region may include cryogenically ablating the tissue region with the expandable element; delivering radiofrequency ablation energy through the mesh; and/or delivering electroporating pulsed energy through the mesh. The method may include assessing contact between at least a portion of the mesh and the tissue region; ablating at least a portion of the tissue region by dispersing a coolant inside the expandable element, and/or manipulating a direction of the coolant dispersion based at least in part on the assessed contact. Positioning the medical device adjacent the tissue region may include advancing the medical device along a guide wire, and the substantially continuous tissue region may include an atrial wall.

A method of treating a tissue site is provided, including freezing at least a portion of the tissue site; and inducing irreversible electroporation of an unfrozen portion of the tissue site. Freezing at least a portion of the tissue site may be achieved by positioning an expandable element into thermal communication with the tissue site and circulating a coolant through an interior of the expandable element, and/or inducing irreversible electroporation may include positioning an electrically-conductive portion of a mesh adjacent the tissue site, and delivering energy pulses to at least a portion of the tissue site with the mesh. The method may also include reversibly cooling at least a portion to the tissue site; and measuring an electrical signal of the tissue site.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein.

DETAILED DESCRIPTION OF THE INVENTION

Figure 1:
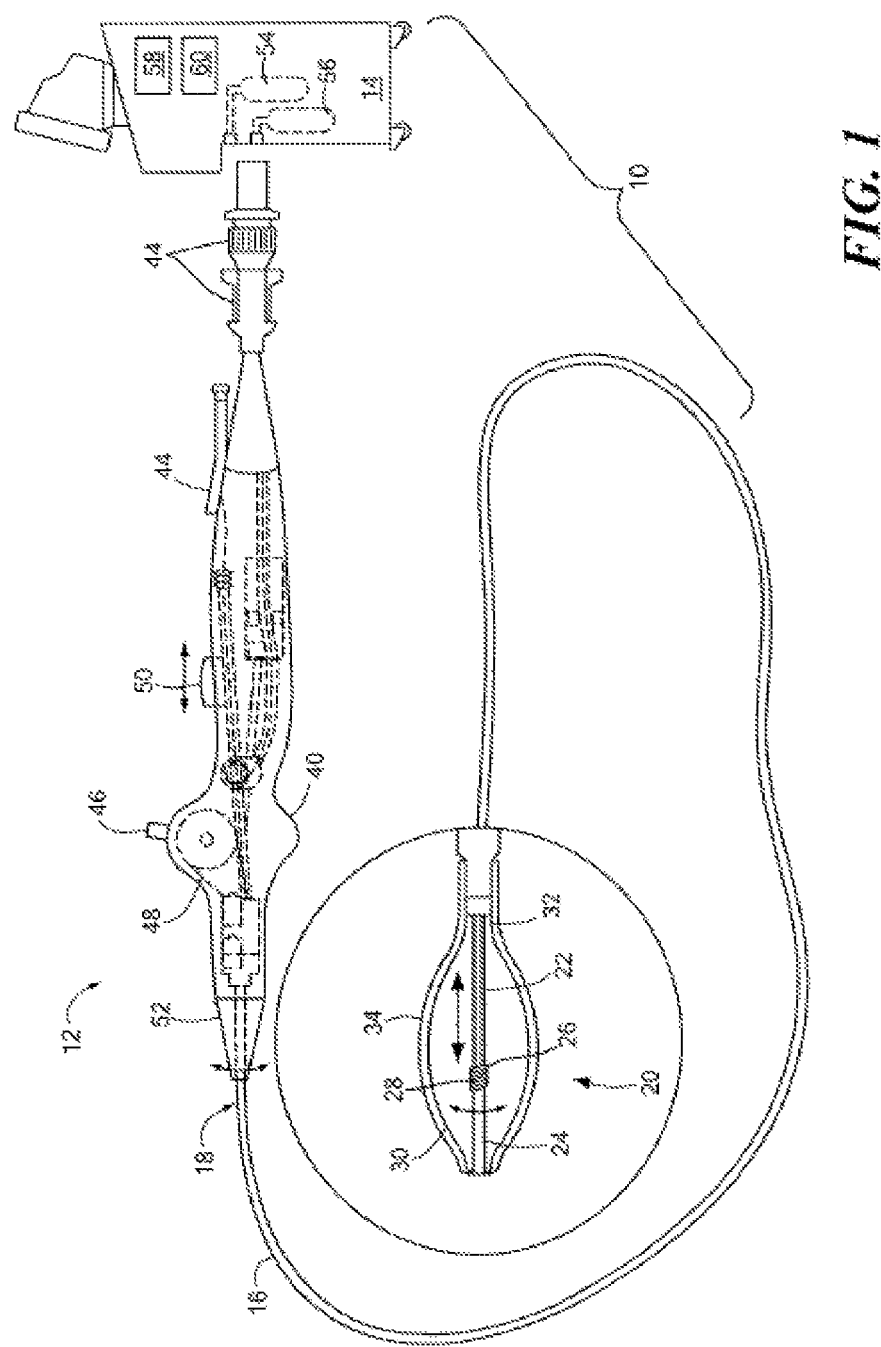
FIG. 1 is an illustration of an example of a medical system constructed in accordance with the principles of the present invention.

The present invention advantageously provides methods and systems for diagnosing aberrant electrical pathways, treating those detected pathways, and verifying the position, contact, and/or orientation of the system. Referring now to the drawing figures in which like reference designations refer to like elements, an embodiment of a medical system constructed in accordance with principles of the present invention is shown in FIG. 1 and generally designated as "10." The system 10 generally includes a medical device 12 that may be coupled to a control unit 14 or operating console. The medical device 12 may generally include one or more diagnostic or treatment regions for energetic, therapeutic and/or investigatory interaction between the medical device 12 and a treatment site. The treatment region(s) may deliver, for example, cryogenic therapy, radiofrequency energy, electroporation treatment or other energetic transfer with a tissue area in proximity to the treatment region(s), including cardiac tissue.

Now referring to FIG. 1, the medical device 12 may include an elongate body 16 passable through a patient's vasculature and/or proximate to a tissue region for diagnosis or treatment, such as a catheter, sheath, or intravascular introducer. The elongate body 16 may define a proximal portion 18 and a distal portion 20, and may further include one or more lumens disposed within the elongate body 16 thereby providing mechanical, electrical, and/or fluid communication between the proximal portion of the elongate body 16 and the distal portion of the elongate body 16, as discussed in more detail below.

The medical device 12 may include a shaft 22 at least partially disposed within a portion of the elongate body 16. The shaft 22 may extend or otherwise protrude from a distal end of the elongate body 16, and may be movable with respect to the elongate body 16 in longitudinal and rotational directions. That is, the shaft 22 may be slidably and/or rotatably moveable with respect to the elongate body 16. The shaft 22 may further define a lumen 24 therein for the introduction and passage of a guide wire and/or a treatment or diagnostic instrument (not shown).

The medical device 12 may further include a fluid delivery conduit 26 traversing at least a portion of the elongate body 16 and towards the distal portion. The delivery conduit 26 may be coupled to or otherwise extend from the distal portion of the elongate body 16, and may further be coupled to the shaft 22 and/or distal tip of the medical device 12. The fluid delivery conduit 26 may define a lumen therein for the passage or delivery of a fluid from the proximal portion of the elongate body 16 and/or the control unit 14 to the distal portion and/or treatment region of the medical device 12. The fluid delivery conduit 26 may further include one or more apertures or openings therein, to provide for the dispersion or directed ejection of fluid from the lumen to an environment exterior to the fluid delivery conduit 26. For example, the fluid delivery conduit 26 may define one or more ports or valves 28 movably positionable with respect to the shaft 22 and/or elongate body 16. The fluid delivery conduit 26 and the port(s) 28 may be both rotatable about the shaft 22 and/or longitudinal axis of the elongate body 16, and may further be longitudinally positionable or slidable along the at least a portion of the length of the shaft 22 and/or elongate body 16. The rotational and slidable orientation of the fluid delivery conduit 26 allows for the controlled, directional dispersion of fluid from the delivery conduit 26 towards a particular segment or region of the medical device 12, as described in more detail herein.

The medical device 12 may further include one or more expandable elements 30 at the distal portion of the elongate body 16. The expandable element 30 may be coupled to a portion of the elongate body 16 and also coupled to a portion of the shaft 22 to contain a portion of the fluid delivery conduit 26 therein. The expandable element 30 defines an interior chamber or region that contains coolant or fluid dispersed from the fluid delivery conduit 26, and may be in fluid communication with an exhaust lumen 32 defined by or included in the elongate body 16 for the removal of dispersed coolant from the interior of the expandable element 30. The expandable element 30 may further include one or more material layers providing for puncture resistance, radiopacity, or the like, and may also be substantially electrically insulative.

Figure 2:
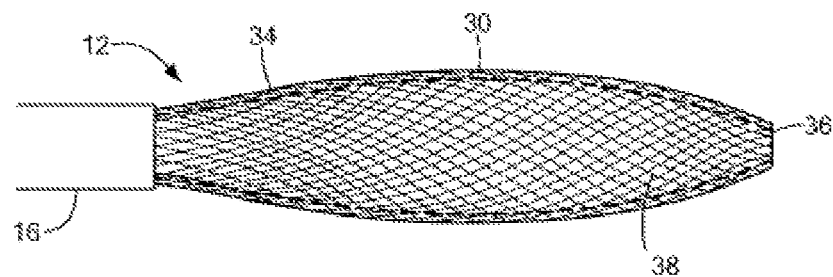
FIG. 2 is an illustration of a distal portion of a medical device of the system of FIG. 1.
Figure 3:
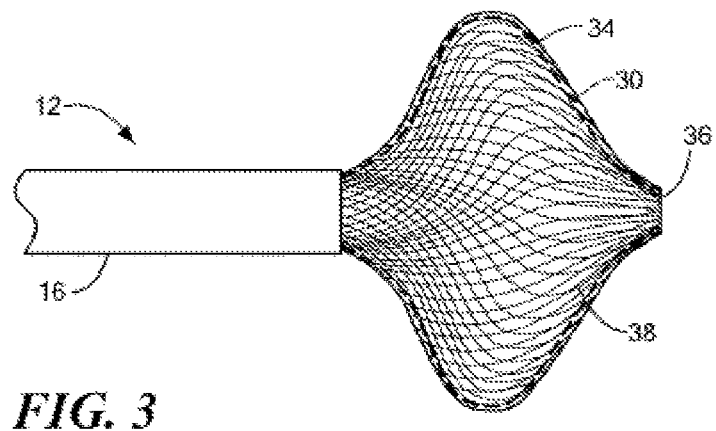
FIG. 3 is another illustration of a distal portion of a medical device of the system of FIG. 1.

Now referring to FIGS. 1-4, the medical device 12 may further include an expandable mesh 34 coupled to the distal portion of the elongate body 16. The mesh 34 may be configurable into a plurality of geometric configurations, such as those shown in FIGS. 2-4. The mesh 34 may define an interwoven wire structure, and may be constructed from a combination of elastic materials, non-elastic materials, and/or shape-memory materials, such as a nickel-titanium alloy or the like, for example. A particular geometric configuration of the mesh 34 may be achieved through the application of mechanical force, thermal energy, and/or electrical energy. For example, the mesh 34 may be predisposed and/or biased towards a first geometric configuration, which may include a substantially elongated, cylindrical shape as shown in FIG. 2. Upon the application of a particular mechanical, thermal, and/or electrical force, the mesh 34 may be selectively transitioned from the first geometric configuration to a second geometric configuration, having a substantially spherical shape, for example, as shown in FIG. 3.

The mesh 34 may define a substantially continuous distal face or surface 36 that defines the distal-most point or contact region of the medical device 12. This is in contrast to prior art devices that have a rigid distal tip or protrusion at a distal end that prevents positioning a distal face or surface of a balloon or expandable element of the device against a substantially continuous tissue region, such as an atrial wall. With regards to the medical device 12, the absence of any such protruding, rigid distal tip or components allows the distal face 36 of the mesh 34 and the expandable element 30 to be placed directly against a tissue region without risking unintended injury to the tissue that a distal protrusion could otherwise inflict, and further allows enhanced contact across a wider area of tissue, resulting in better electrical and/or thermal communication than would otherwise be possible. The distal face 36 may include an opening allowing the exit of a guidewire or other instrument from the lumen in the shaft 22, but the opening may be substantially planar or contiguous with the portion of the mesh 34 and/or expandable element 30 immediately surrounding the opening such that the shaft 22 and/or any interfacing component, washer, or the like between the mesh 34, expandable element 30, and/or the shaft 22 has a minimal affect on the positioning of the distal face 36 of the mesh 34 against a tissue wall or region.

Of note, although first and second geometric configurations are described above and shown in FIGS. 2-3, it is contemplated that a mesh 34 having more than two configurations may be employed and achieved through a combination of mechanical, thermal, and/or electrical forces, as well as through characteristics provided through material selection in the construction of the shaping element. Moreover, while examples and illustrations of particular geometric configurations have been provided, it is understood that virtually any shapes, configurations, and/or dimensions may be included and/or achieved by the medical device 12 of the present invention, including but not limited to those shapes illustrated and described herein. A particular geometric configuration may include circular, conical, concave, convex, rounded, or flattened features and/or combinations thereof. Accordingly, an embodiment of the medical device 12 of the present invention may be able to provide focal lesions, circular lesions, linear lesions, circumferential lesions, and combinations thereof.

At least a portion of the mesh 34 may be electrically conductive to provide the ability to convey an electrical signal, current, or voltage to a designated tissue region and/or for measuring, recording, or otherwise assessing one or more electrical properties or characteristics of surrounding tissue. Portions of the mesh 34 may be electrically insulated, while other portions of the mesh 34 may be exposed and thus conductive of an electrical signal to facilitate contact and or use of the medical device 12 in targeted physiological areas. For example, conductive portions of the mesh 34 may be positioned at discrete locations about the expandable element 30, and may surround or encircle substantially all or only a fractional portion of the expandable members. Conductive portions of the mesh 34 may be asymmetrically disposed about the expandable member 30, e.g., positioned predominantly towards the proximal or distal portions of the expandable member 30, and/or on a side of the expandable member 30 likely to face a contacted tissue area.

Figure 4:
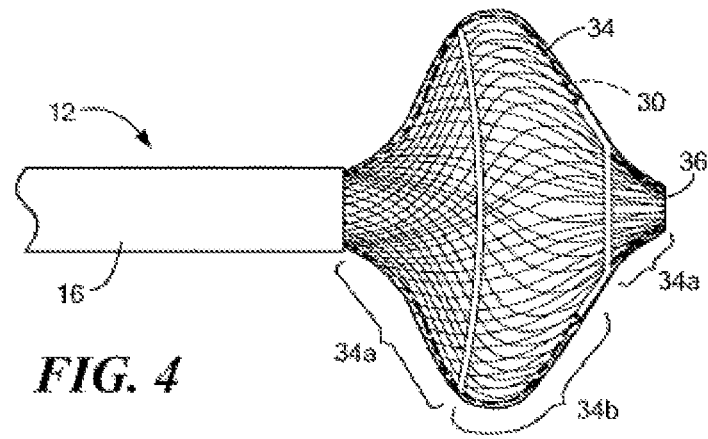
FIG. 4 is an illustration of a partially-insulated distal portion of a medical device of the system of FIG. 1.

For example, as shown in FIG. 4, the mesh 34 may include insulated portions 34*a* on a proximal and/or distal region of the mesh 34, with an electrically-conductive portion 34*b* disposed between the insulated portions 34*a*. The proximal insulated portion 34*a* may be typically positioned away from a tissue site being treated or diagnosed, and thus may be insulated to direct diagnostic and/or treatment operations to a more distal conductive portion 34*b*. Should a second, distal-most insulated or otherwise non-electrically conductive portion 34*a* of the mesh 34 also be included, the resulting conductive "band" may be used to target or treat a surrounding lumen wall or surface, such as that of a vascular pathway or vessel.

Figure 5:
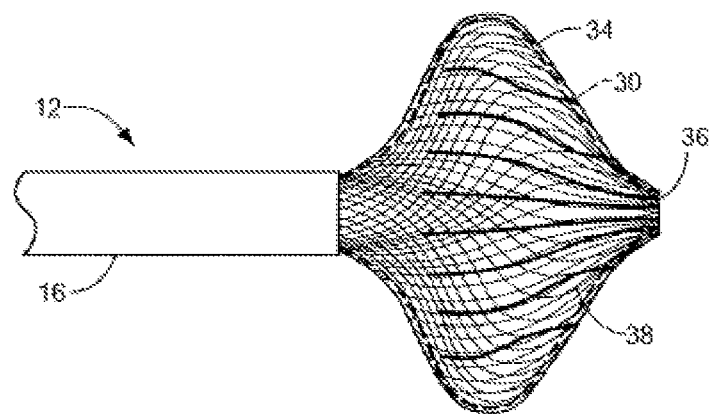
FIG. 5 is another illustration of a partially-insulated distal portion of a medical device of the system of FIG. 1.

Turning to FIG. 5, the mesh 34 may be segmented into a plurality of discrete conductive regions 34*b* divided by a plurality of insulated or non-conductive portion 34*a*. The conductive regions 34*b* may be oriented substantially parallel to a longitudinal axis of the medical device, i.e., in a distal-to-proximal direction. The divided segments may provide for selective operation or activation of one or more subsets of the plurality of conductive regions. Such selective operation may allow selectively focused treatment or diagnosis when a targeted tissue site is only in contact with a portion of the mesh 34, for example. Further, the insulatively-delineated conductive portions 34b may be operated in a bipolar manner to conduct current through tissue along pathways transverse to the longitudinal axis of the medical device 12 between adjacent or otherwise spaced conductive portion 34b of the mesh 34.

Figure 6:
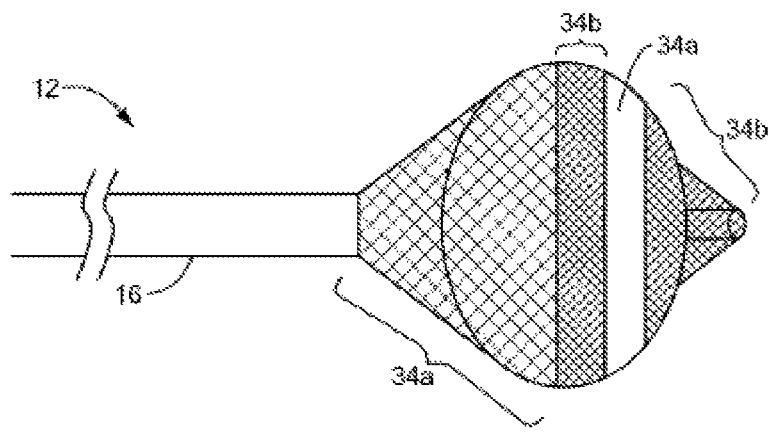
FIG. 6 is still another illustration of a partially-insulated distal portion of a medical device of the system of FIG. 1.

Referring now to FIG. 6, the medical device may include an electrically insulated portion 34a disposed between two conductive portions 34b of the mesh 34. The divided conductive portions may be selectively operated or activated to treat tissue that is only adjacent one of the regions. For example, the medical device 12 may be passed through a tissue wall (such as a cardiac septal wall), then pulled proximally such that a proximal portion of the mesh 34 can treat and/or diagnose the contacted portion of the septal wall without activation of the distal portion of the mesh 34. Further, the conductive portions 34b may be operated in a bipolar manner to conduct current around the insulated portion 34a and through tissue along pathways substantially parallel to the longitudinal axis of the medical device 12 between adjacent or otherwise spaced conductive portion 34b of the mesh 34.

The exposed or otherwise electrically conductive portions of the mesh 34 may be present at one or more junctions 38 between the interwoven or intersecting wires that define the mesh 34. The junctions 38 may present a plurality of conductive points or measurement locations on the medical device 12 for use in assessing or treating a targeted tissue area. For example, each junction 38 may be electrically coupled to an output portion of a radiofrequency or electrical signal generator (such as that described below), and each junction 38 may also include or define a sensor, such as a thermocouple, an electrical conductivity sensor, a spectrometer, a pressure sensor, a fluid flow sensor, a pH sensor, and/or a thermal sensor (not shown) coupled to or in communication with the control unit 14 to trigger or actuate changes in operation when predetermined sequences, properties, or measurements are attained or exceeded.

Figure 7:
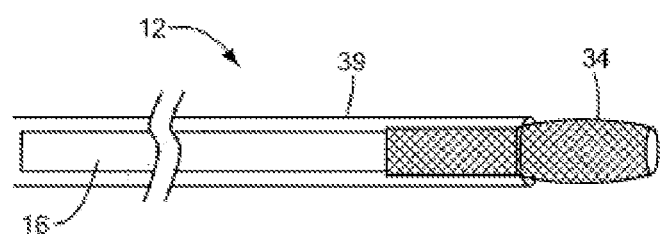
FIG. 7 is an illustration of a sheathed distal portion of a medical device of the system of FIG. 1.

Turning now to FIG. 7, the medical device 12 may include a sheath 39 slidably positionable over at least a portion of the mesh 34 and elongate body 16. The mesh 34 may be controllably manipulated into a desired position by one or more controls at a proximal end of the medical device 12, and may further be positioned to maintain a desired deployment or expansion of the mesh 34. The sheath 39 may further provide an insulative cover over a portion of the mesh 34 to inhibit electrical signal conduction and/or thermal energy transfer between the covered portion of the mesh 34 and the surrounding environment.

Figure 8:
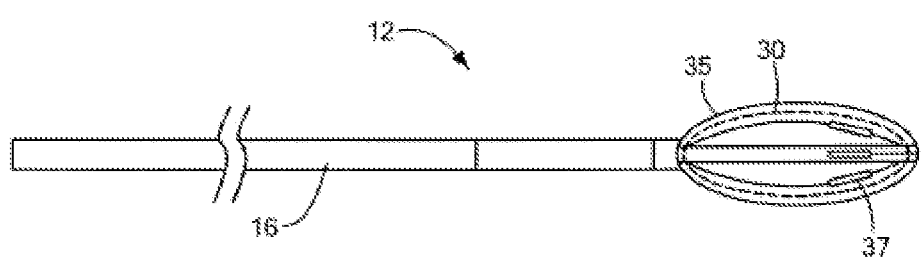
FIG. 8 is an illustration of another example of a distal portion of a medical device for use with the system of FIG. 1.

Referring now to FIG. 8, the distal portion 20 of the medical device 12 may include one or more longitudinally-oriented, deployable arms or splines 35 movably coupled to the elongate body 16, where one or more of the arms 30 may include one or more electrically conductive surface(s) and/or electrode(s) 37 to deliver or conduct electrical pulses to a designated treatment area. The arms 35 may be disposed around a circumference of the elongate body 16 and/or the expandable element 30, and may be controllably moved to manipulate an expansion or radial distance between the arms 35 and the elongate body 16. The selectively adjustable radius of the arms 35 allows engagement and subsequent diagnosis or treatment of varying anatomical tissue structures which may include different geometries or dimensions. For example, arms 35 may be expanded to contact a larger radius or portion of a tissue wall or structure, or alternatively, may be manipulated into a smaller radius to engage a vessel or lumen tissue structure having a smaller diameter. During operation, the expandable element 30 may be expanded within the space between the splines or arms 35, which forces energy to preferentially pass into and through the endocardium which is in contact with the conductive portions of the splines, and also prevents energy loss into the surrounding blood pool or flow.

Referring again to FIG. 1, the medical device 12 may include a handle 40 coupled to the proximal portion of the elongate body 16. The handle 40 can include circuitry for identification and/or use in controlling of the medical device 12 or another component of the system 10. Additionally, the handle 40 may be provided with a fitting 42 for receiving a guide wire or another diagnostic/treatment instrument that may be passed into the lumen 24 of the shaft 22. The handle 40 may also include connectors 44 that are matable to the control unit 14 to establish communication between the medical device 12 and one or more components or portions of the control unit 14.

The handle 40 may also include one or more actuation or control features that allow a user to control, deflect, steer, or otherwise manipulate a distal portion of the medical device 12 from the proximal portion of the medical device 12. For example, the handle 40 may include one or more components such as a lever or knob 46 for manipulating the elongate body 16 and/or additional components of the medical device 12. For example, a pull wire 48 with a proximal end and a distal end may have its distal end anchored to the elongate body 16 at or near the distal portion. The proximal end of the pull wire 48 may be anchored to an element such as a cam in communication with and responsive to the lever 46. The medical device 12 may include an actuator element 50 that is movably coupled to the proximal portion of the elongate body 16 and/or the handle 40 for the manipulation and movement of a portion of the medical device 12, such as the shaft 22, the fluid delivery conduit 26, the expandable element 30, and/or the mesh 34, for example. The actuator element 50 may include a thumb-slide, a push-button, a rotating lever, or other mechanical structure for providing a movable coupling to the elongate body 16, the handle 40, and/or the shaft 22. Moreover, the actuator element 50 may be movably coupled to the handle 40 such that the actuator element 50 is movable into individual, distinct positions, and is able to be releasably secured in any one of the distinct positions.

The medical device 12 may include one or more rotational control elements 52 that are rotatably coupled to the proximal portion of the fluid delivery conduit 26, shaft 22 and/or the handle 40 such that rotating the rotational control element 52 about a longitudinal axis of the handle 40 and/or elongate body 16 results in similar rotation of the shaft 22 and/or the fluid delivery conduit 26 at the distal portion of the medical device 12. The rotational control element 52 may include a knob, dial, or other mechanical structure for providing a rotatable coupling to the elongate body 16, the handle 40 and/or the shaft 22. Moreover, the rotational control element 52 may be rotatably coupled to the handle 40 and/or elongate body 16 such that the rotational control element 52 is movable into individual, distinct positions, and is able to be releasably secured in any one of the distinct positions.

Manipulation of the actuator element(s) 50 and/or the rotational control element(s) 52 provides for movement of the fluid delivery conduit 26 to direct dispersed coolant or fluid flow onto a particular segment or region of the expandable element 30 for the desired clinical or therapeutic effect.

In addition, the actuator element(s) 50 and/or rotational control element(s) 52 can be used to controllably position and/or rotate the shaft 22 of the medical device 12, which, in turn, can be used to achieve a desired shape, expansion, or orientation of the mesh 34.

The system 10 may include one or more treatment or diagnostic sources coupled to the medical device 12 for use in an operative procedure, such as tissue ablation, for example. The control unit 14 may include a fluid supply 54 including a coolant, cryogenic refrigerant, or the like, an exhaust or scavenging system 10 (not shown) for recovering or venting expended fluid for re-use or disposal, as well as various control mechanisms. In addition to providing an exhaust function for the fluid or coolant supply, the control unit 14 may also include pumps, valves, controllers or the like to recover and/or re-circulate fluid delivered to the handle 40, the elongate body 16, and/or the fluid pathways of the medical device 12. A vacuum pump 56 in the control unit 14 may create a low-pressure environment in one or more conduits within the medical device 12 so that fluid is drawn into the conduit(s)/lumen(s) of the elongate body 16, away from the distal portion and towards the proximal portion of the elongate body 16.

The control unit 14 may include a treatment energy source 58 as a treatment or diagnostic mechanism in communication with one or more portions of the mesh 34 of the medical device 12. The treatment energy source 58 may include an electrical current or pulse generator, a radiofrequency generator or the like having a plurality of output channels, with each channel coupled to an individual junction and/or electrode(s) 37. The treatment energy source 58 may be operable in one or more modes of operation, including for example: (i) bipolar energy delivery between at least two electrodes or electrically-conductive portions of the medical device 12 within a patient's body, (ii) monopolar or unipolar energy delivery to one or more of the electrodes or electrically-conductive portions on the medical device 12 within a patient's body and through a patient return or ground electrode (not shown) spaced apart from the electrodes of the medical device 12, such as on a patient's skin, in the pericardial space, on an independently movable guide wire, or on an auxiliary device in another region or vessel of the patient, for example, and (iii) a combination of the monopolar and bipolar modes.

The treatment energy source 58 may provide electrical pulses to the medical device 12, such as the mesh 34 or electrically conductive portions thereof and/or the electrodes 37, to perform an electroporation procedure. "Electroporation" utilizes high density, short (e.g., microsecond to millisecond) electrical pulses to effectuate a physiological modification (i.e., permeabilization) of the cells to which the energy is applied. In particular, the pulsed energy induces the formation of microscopic pores or openings in the cell membrane. Depending upon the characteristics of the electrical pulses, an electroporated cell can survive electroporation (i.e., "reversible electroporation") or die (i.e., irreversible electroporation, "IEP"). Conventionally, reversible electroporation has been used to transfer agents into targeted cells for various purposes.

The treatment energy source 58 may be configured and programmed to deliver pulsed, high voltage density, pulsed energy as described below, appropriate for achieving desired pulsed, high voltage ablation (or IEP ablation). As a point of reference, the pulsed, high voltage ablation effects of the present disclosure are distinguishable from DC current ablation, as well as thermally-induced ablation attendant with conventional RF techniques. The IEP in accordance with the present disclosure is sufficient to induce cell death for purposes of completely blocking an aberrant conductive pathway along or through cardiac tissue, destroying the ability of the so-ablated cardiac tissue to propagate or conduct an electrical signal.

To that end, the treatment energy source 58 may deliver a number of different various waveforms or shapes of pulses to achieve electroporation ablation of cardiac tissue, including sinusoidal AC pulses, DC pulses, square wave pulses, exponentially decaying waveforms, or other pulse shapes such as combined AC/DC pulses, or DC shifted signals. The parameters of pulsed energy generated by the treatment energy source 58 can vary in one or more of the following manners: waveform shape, pulse polarity, amplitude, pulse duration, interval between pulses, number of pulses (frequency), combination of waveforms, etc. One or more of these parameters can be altered or changed during the ablation procedure. For example, the treatment energy source 58 may be adapted to generate a high density energy gradient in the range of 10-1,000 V/cm, pulsed at rates on the order of 1-1,000 microseconds. The voltage level, pulse rate, waveform, and other parameters can be varied as described below, with the control unit including, in some embodiments, a controller that automatically dictates operational parameters as a function of one or more characteristics of the cardiac tissue target site (e.g., tissue type (such as fatty tissue, thickness, cell orientation, naturally-occurring electrical activity, etc.)).

The treatment energy source 58 may be configured to deliver biphasic electrical pulses to one or more portions of the mesh and/or the medical device. As a point of reference, while monophasic electrical pulses may alternatively be employed, the application of biphasic electrical pulses has surprisingly been found to produce unexpectedly beneficial results in the context of cardiac tissue ablation. With biphasic electroporation pulses, the direction of the pulses completing one cycle alternates in less than a few hundred microseconds. As a result, the cells to which the biphasic electrical pulses are applied undergo alternation of electrical field bias. With IEP cardiac tissue ablation, changing the direction of bias surprisingly helps to reduce prolonged post-ablation depolarization and/or ion charging. As a result, it reduces prolonged muscle excitation (e.g., skeletal and cardiac cells) and risks of post shock fibrillation of the cardiac cells. Further, biphasic electrical pulses overcome the high impedance characteristics of fatty cells often times associated with cardiac ablation procedures. Thus, biphasic electrical pulses avoid the possible drawbacks of monophasic electrical pulses including: 1) atrial or ventricular fibrillation, 2) less effective in making lesions through fat, 3) propensity to make thermal lesions on the anode side of an electrode pair, and 4) prolonged muscle excitation.

With respect to biphasic energy (i.e., half positive phase and half negative phase), the treatment energy source 58 may be programmed to deliver a plurality of pulses each having a cycle time of not more than 5 milliseconds, but preferably not more than 50 microseconds; an output voltage between approximately 200-2000 volts, preferably between 500 and 1000 volts at a pulse width between approximately 0.005 microseconds-5 milliseconds, preferably between 0.005 microseconds and 50 microseconds; and/or a series of pulse trains, with each train having between approximately 1-500 monophasic or biphasic pulses, preferably 10-100 pulses. The pulses may include a plurality.

The system 10 may further include one or more sensors to monitor the operating parameters throughout the system 10, including for example, pressure, temperature, flow rates, volume, power delivery, impedance, or the like in the control unit 14 and/or the medical device 12, in addition to monitoring, recording or otherwise conveying measurements or conditions within the medical device 12 or the ambient environment at the distal portion of the medical device 12. The sensor(s) may be in communication with the control unit 14 for initiating or triggering one or more alerts or therapeutic delivery modifications during operation of the medical device 12. One or more valves, controllers, or the like may be in communication with the sensor(s) to provide for the controlled dispersion or circulation of fluid through the lumens/fluid paths of the medical device 12. Such valves, controllers, or the like may be located in a portion of the medical device 12 and/or in the control unit 14.

The control unit 14 may include one or more controllers, processors, and/or software modules containing instructions or algorithms to provide for the automated operation and performance of the features, sequences, calculations, or procedures described herein. For example, the control unit 14 may include an impedance measurement module or signal processing unit 60 to measure one or more impedance characteristics between the selected portions or regions of the mesh 34, such as individual junctions. An excitation current may be applied between one or more of the junctions 38 on the medical device 12 and/or a patient return electrode, and the resulting impedance may be measured and recorded at multiple locations of the mesh 34. Measured impedance values can vary depending on the type of tissue in the electrically conductive pathway resulting in the measured impedance. For example, a measured impedance value for an electrical path through a blood stream is significantly different from an impedance measurement taken through a contacted cardiac tissue wall. The resulting measurements or recordings can thus be used to assess whether specific portions of the mesh 34 are in contact with a targeted tissue area, and the resulting treatment may be modified accordingly based on the assessed contact to direct therapeutic or treatment energies or methods towards the contacted sector or region of the device 12.

In an exemplary use of the medical system 10, the distal portion 20 of the medical device 12 may be positioned in proximity to a tissue region to be treated. In particular, a portion of the mesh 34 and/or the electrically conductive portions of the arms 35 may be positioned to contact a tissue region, such as a substantially continuous portion of an atrial wall, a circumference of a blood vessel, or the like. The mesh 34, arms 35 and/or expandable element 30 may be manipulated into a desired geometric configuration. For example, the expandable element 30 may be inflated within the mesh 34 or arms 35, thereby conforming to the shape of mesh 34 or the arms 35. As such, irrespective of whether the expandable element 30 has a particular shape or dimensional capacity, the mesh 34 or arms 35 may be used to provide a restraining or confining guide and/or "shell" within which the expandable element 30 may be inflated to ensure a desired geometric configuration and/or a desired volume. In addition, the sheath may be manipulated to affect the expansion or deployment of at least a portion of the mesh 34 and the expandable element 30 therein.

The mesh 34 or arms 35 may be employed to determine a region of contact between the mesh 34 or arms 35 and the surrounding tissue. For example, the electrically-conductive portions of the mesh 34 or arms 35 may be used to measure a plurality of impedance values around the circumference and length of the mesh 34 or arms 35 for a contact assessment between the device and the tissue. The impedance measurements can be taken at individual junctions or electrodes 37, which may each have an independent channel for communicating with the control unit 14. Those portions of the mesh 34 (such as one or more discrete junctions) or arms 35 identified having the greatest contact with the targeted tissue can be identified based on the impedance values, and subsequently used to target or direct therapeutic and/or diagnostic energies towards the contacting region or sector of the device. Alternatively, the medical device 12 may be repositioned or realigned until the contact assessment indicates a desired portion of the mesh 34 is in contact with a particular tissue segment.

The electrically-conductive portions of the mesh 34, such as the exposed or un-insulated junctions 38, or the electrodes 37 on the arms 35, may be used to measure and/or record electrical signals or conduction pathways in the contacted tissue region, commonly referred to as "mapping." The targeted tissue region may be mapped to identify the location of abnormal signal pathways for subsequent therapy or treatment. Further, regions of tissue identified or suspected of having such aberrant electrical activity may be temporarily electrically inhibited by reducing the temperature of the tissue. In particular, a coolant may be circulated through the expandable element 30, thus cooling tissue in proximity to the expandable element. The surrounding tissue may be cooled to a temperature that temporarily prevents or reduces electrical conduction without destroying or ablating the affected tissue—e.g., "cryo-mapping." Subsequent electrical measurement may be taken with the medical device 12 to confirm that the cryomapped segment should be treated further through the application of one or more ablative techniques.

Once attaining the desired position, contact assessment, and/or confirmation that a tissue site is problematic, the medical device 12 may be used to treat the contacted tissue area. For example, the expandable element 30 of the medical device 12 may be subjected to a fluid flow, including a cryogenic coolant or the like, to create an ablative lesion within a desired tissue region. The expandable element 30 may be inflated such that portions of the expandable element 30 protrude through the mesh 34 or arms 35 to contact and/or be in position to thermally affect the desired tissue region, while substantially retaining the geometric configuration of the mesh 34 or arms 35. The coolant may be controllably delivered through the fluid delivery conduit 26 and directed towards the particular portion of the mesh 34 or expandable element 30 indicated as having the greatest contact with the tissue. The manipulation of the fluid delivery conduit 26 may be achieved through manipulating one or more actuators on the handle 40, and may further be facilitated by visualizing one or more positional or orientation markers (not shown) on a distal part of the delivery conduit 26 through medical imaging means, such as fluoroscopy or the like.

In addition and/or alternatively to cryogenically treating the targeted tissue region, one or more portions of the mesh 34 or arms 35 may be used to conduct radiofrequency energy or electrical pulses into the tissue to create one or more ablation zones in the tissue. The radiofrequency energy may be delivered to the specific junctions or electrodes identified as being in contact with the tissue. The radiofrequency energy may be delivered independently, simultaneously, and/or sequentially with the delivery of the cryogenic fluid flow through the expandable element 30 to achieve the desired clinical effect.

In addition, the medical device may be operated to deliver electroporating energy pulses through the conductive portions of the mesh 34 or arms 35 to achieve IEP of the targeted tissue using one or more of the energy delivery characteristics described above. For example, a string of biphasic pulses may be delivered over 5 seconds, with each train or train segment comprised of 40 pulses over 8 milliseconds at a frequency of 1 Hz effect ablation of the targeted cardiac tissue by IEP. Exemplary pulse trains may include a biphasic pulse width and inter-pulse interval of 100 microseconds, for example. Other biphasic waveforms can also be employed, having differing parameters such as shapes, amplitudes, pulse duration, interval between pulses, combination of pulses, etc. For example, biphasic energy pulses may be applied at very short durations (on the order of 1 nanosecond-50 microseconds, up to 100 microseconds, in some embodiments in the range of 50-200 microseconds) to effectively ablate fatty areas of heart tissue. Further, trains of short biphasic pulses having low amplitude can be effective in the permeabilization of cells while minimizing thermal damage. Such delivered biphasic pulse trains may be provided over a range of 2-6 seconds, each train having 20-60 biphasic pulses, each pulse having a cycle time of not more than 5 milliseconds, but preferably not more than 50 microseconds; an output voltage between approximately 200-2000 volts, preferably between 500 and 1000 volts at a pulse width between approximately 0.005 microseconds-5 milliseconds, preferably between 0.005 microseconds and 50 microseconds; and/or a series of pulse trains, with each train having between approximately 1-500 monophasic or biphasic pulses, preferably 10-100 pulses. Delivery of energy pulse trains are preferably timed to correspond with the onset of depolarization of the myocardium. Alternately the pulse trains may be delivered to myocardium that is fully polarized, just before normal sinus rhythm activation occurs. By employing pulsed, high voltage energy to effectuate IEP ablation of cardiac tissue cells, transmural lesions can be rapidly created at rates much less than those typically encountered with conventional radiofrequency ablation. Further, the applied current can be specifically directed to create very specific lesion patterns without the generation of excessive heat.

One or more treatment modalities may be combined through the use of the medical device 12 to achieve the desired effect. For example, electroporation treatment may be combined with cryogenic treatment to achieve a synergistic affect facilitating deeper and more continuous tissue treatment. For example, a cryogenic coolant may be circulated through the expandable element 30, which results in thermal exchange with the surrounding tissue to create frozen tissue regions.

During the cooling of the expandable element 30 and thus portions of the targeted tissue region, one or more portions of the mesh 34 or arms 35 may be powered by the energy treatment source 58 to deliver electroporating pulses between one or more regions of the mesh 34 and/or arms 35 and a reference or patient electrode on or in the patient. Electrical conduction through the frozen tissue is significantly reduced or altogether eliminated, and accordingly, electrical current paths between the activated portions of the mesh 34 or arms 35 flow around the frozen tissue regions, thus driving the current paths deeper into the targeted tissue area. By controllably increasing the cooling rate of the expandable element 30 (via the control unit 14, for example) while also correspondingly adjusting the power delivery to the mesh 34 or arms 35, increased tissue depths can be frozen, thus driving the current paths even deeper into the target tissue region, resulting in a deeper, potentially more effective tissue lesion or ablation site. The combined operation of the expandable element 30 and the mesh 34 or arms 35 takes advantage of the electrical isolation property of frozen tissue, by freezing the tissue between electrically conductive portions of the mesh and/or a ground electrode and forcing the provided electroporating, pulsed energy to travel deeper in the periphery of the frozen tissue and promote deeper tissue destruction and ablation.

Moreover, Cryogenic ablation through the expandable element is effective when good tissue contact is achieved when ablating about a great vessel ostium. In locations about the ostium where blood flow is not occluded by contact of the expandable element, the tissue may not become frozen. This also creates an inhomogeneity of tissue electrical conductivity about the targeted ostial ablation circumference. The frozen tissue is electrically insulative and the non-frozen portions remain electrically conductive. Exemplary uses of the combined cryogenic and electrical energy delivery, described above, can also take advantage of the two complimentary modes of cryogenic and electroporative ablation to produce contiguous circumferential lesions. In the regions that are unable to be frozen and cryogenically ablated, the electroporation energy passes preferentially, such that these regions become ablated by this alternate energy mode.

The cardiac tissue ablation systems and methods of the present disclosure provide a marked improvement over previous applications. The IEP energy delivery may be performed with a series of microsecond or nanosecond duration, high voltage pulses. The delivery is non-thermal so heat-sink issues encountered with conventional thermal ablations are eliminated. A focal irrigated, radiofrequency ablation procedure typically requires approximately 35-45 minutes of actual energy delivery time. During that time, over a liter of saline may be infused into the patient to cool an RF electrode. A cryogenic ablation procedure typically requires approximately 30 minutes of cryogenic application time. In stark contrast, the duration of IEP energy delivery could be approximately 2-5 seconds. This is a major reduction in time required to perform a procedure. In addition, it eliminates the risk of complications such as esophageal fistulae, pulmonary vein stenosis, and phrenic nerve palsy. This results in a procedure to treat paroxysmal AF that could be accomplished in less than an hour, without the risk of the most feared complications. Additionally, IEP ablation does not require saline irrigation to cool the electrodes. This eliminates the problem of fluid overload in fluid compromised patients during an atrial fibrillation ablation procedure. Further, radiofrequency ablation may disrupt the cardiac endothelial surface, activate the extrinsic coagulation cascade, and lead to char and thrombus formation, which in turn may lead to systemic thromboembolism—all of which IEP avoids It will be appreciated by persons skilled in the art that the present invention is not limited to what has been particularly shown and described herein above. In addition, unless mention was made above to the contrary, it should be noted that all of the accompanying drawings are not to scale. A variety of modifications and variations are possible in light of the above teachings without departing from the scope and spirit of the invention, which is limited only by the following claims.

What is claimed is:

1. A method of treating a substantially continuous tissue region, the method comprising:
   positioning a medical device adjacent the tissue region, the medical device including:
   a catheter body;
   an expandable element; and an electrically conductive mesh substantially enclosing the expandable element, the mesh having:
a proximal portion coupled to the catheter body, the proximal portion being electrically insulated;
a distal portion coupled to the elongate body, the distal portion of the mesh being electrically conductive and defining a distal face configured to be in contact with the tissue region and the entirety of the distal face configured to deliver ablation energy to the tissue;
a first circumferential portion located between the proximal portion and the distal portion, the first circumferential portion being electrically conductive; and
a second circumferential portion located between the first circumferential portion and the distal portion, the second circumferential portion being electrically insulted;
contacting the substantially continuous tissue region with the distal face of the expandable element;
measuring an electrical signal from the tissue region with the mesh; and
ablating at least a portion of the tissue region with at least one of the expandable element and the mesh.

2. The method of claim 1, wherein ablating at least a portion of the tissue region includes cryogenically ablating the tissue region with the expandable element.

3. The method of claim 1, wherein ablating at least a portion of the tissue region includes delivering radiofrequency ablation energy through the mesh.

4. The method of claim 1, wherein ablating at least a portion of the tissue region includes delivering electroporating pulsed energy through the mesh.

5. The method of claim 1, further comprising assessing contact between at least a portion of the mesh and the tissue region.

6. The method of claim 5, wherein ablating at least a portion of the tissue region includes dispersing a coolant inside the expandable element, and the method further comprises manipulating a direction of the coolant dispersion based at least in part on the assessed contact.

7. The method of claim 1, wherein positioning a medical device adjacent the tissue region includes advancing the medical device along a guide wire.

8. The method of claim 1, wherein the substantially continuous tissue region is an atrial wall.

9. The method of claim 1, wherein the medical device further includes a sheath slidably coupled to at least a portion of the catheter body.

10. A method of treating a tissue region, the method comprising:
positioning a medical device adjacent the tissue region, the medical device including:
a catheter body;
an elongate body disposed in the catheter body;
an expandable element having a proximal portion coupled to the catheter body and a distal portion coupled to the elongate body;
a mesh surrounding the expandable element, the mesh having:
a proximal portion coupled to the catheter body, the proximal portion being electrically insulated;
a distal portion coupled to the elongate body, the distal portion of the mesh being electrically conductive and defining a distal face configured to be in contact with the tissue region and the entirety of the distal face configured to deliver ablation energy to the tissue region;
a first circumferential portion located between the proximal portion and the distal portion, the first circumferential portion being electrically conductive; and
a second circumferential portion located between the first circumferential portion and the distal portion, the second circumferential portion being electrically insulated; and
a coolant source in fluid communication with the expandable element;
contacting the tissue region with the distal face of the mesh;
measuring an electrical signal from the tissue region with the mesh; and
ablating at least a portion of the tissue region with at least one of the expandable element and the mesh.

11. The method of claim 10, wherein ablating at least a portion of the tissue region includes cryogenically ablating the tissue region with the expandable element.

12. The method of claim 10, wherein ablating at least a portion of the tissue region includes delivering radiofrequency ablation energy through the mesh.

13. The method of claim 10, wherein ablating at least a portion of the tissue region includes delivering electroporating pulsed energy through the mesh.

14. The method of claim 10, further comprising assessing contact between at least a portion of the mesh and the tissue region.

15. The method of claim 14, wherein ablating at least a portion of the tissue region includes dispersing a coolant inside the expandable element, and the method further comprises manipulating a direction of the coolant dispersion based at least in part on the assessed contact.

16. The method of claim 10, wherein the mesh includes at least one of a plurality of thermistors and plurality of thermocouples.

* * * * *